US010342516B2

(12) United States Patent
Denk et al.

(10) Patent No.: US 10,342,516 B2
(45) Date of Patent: Jul. 9, 2019

(54) ADAPTIVE ULTRASOUND IMAGE OPTIMIZATION THROUGH AUTOMATIC GAIN CONTROL ADJUSTMENT

(71) Applicant: General Electric Company, Schenectady, NY (US)

(72) Inventors: Stefan Denk, Oberöesterreich (AT); Daniel John Buckton, Oberöesterreich (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 725 days.

(21) Appl. No.: 14/495,427

(22) Filed: Sep. 24, 2014

(65) Prior Publication Data

US 2016/0081662 A1 Mar. 24, 2016

(51) Int. Cl.
*A61B 8/00* (2006.01)
*A61B 8/08* (2006.01)
*G01S 7/52* (2006.01)

(52) U.S. Cl.
CPC .............. *A61B 8/5207* (2013.01); *A61B 8/54* (2013.01); *G01S 7/52033* (2013.01); *A61B 8/461* (2013.01); *A61B 8/467* (2013.01)

(58) Field of Classification Search
None
See application file for complete search history.

(56) References Cited

U.S. PATENT DOCUMENTS

| 5,579,768 | A | | 12/1996 | Klesenski | |
|---|---|---|---|---|---|
| 6,102,859 | A | * | 8/2000 | Mo | .......................... A61B 8/00 600/443 |
| 6,743,174 | B2 | | 6/2004 | Ng et al. | |
| 8,382,669 | B2 | | 2/2013 | Kakee | |
| 8,403,855 | B2 | | 3/2013 | Lee et al. | |
| 2003/0187353 | A1 | * | 10/2003 | Ng | .......................... A61B 8/467 600/437 |
| 2010/0049046 | A1 | | 2/2010 | Peiffer et al. | |
| 2011/0043434 | A1 | * | 2/2011 | Roncalez | ............ G06F 3/04847 345/3.1 |

FOREIGN PATENT DOCUMENTS

EP 2710960 3/2014

* cited by examiner

*Primary Examiner* — Jonathan Cwern

(74) *Attorney, Agent, or Firm* — McAndrews, Held & Malloy, Ltd.; Jacob Groethe; David Bates

(57) ABSTRACT

Various embodiments include systems and methods for gain auto-correction. Automatic gain optimization or correction may be applied in an ultrasound system, during an automatic gain mode. The automatic gain optimization or correction may comprise automatic time gain compensation (TGC) and/or lateral gain compensation (LGC) optimization or correction. The applying of the gain optimization or correction may comprise determining an optimal gain, such as based on processing input ultrasound images; determining, based on the optimal gain, settings for a plurality of user controls of the ultrasound system (e.g., slides, knobs, etc.), corresponding to the optimal gain; and providing feedback to a user of the ultrasound system, relating to (e.g., showing) the settings for the plurality of user controls that correspond to the optimal gain. The plurality of user controls may be adjustable manually and automatically. The user controls may be physical or virtual.

28 Claims, 6 Drawing Sheets

410

Ultrasound image with default TGC

420

Ultrasound image with auto-corrected TGC

Ultrasound image user adjusted TGC

Ultrasound image with auto-corrected TGC

ADAPTIVE ULTRASOUND IMAGE OPTIMIZATION THROUGH AUTOMATIC GAIN CONTROL ADJUSTMENT

CLAIMS OF PRIORITY

[Not Applicable]

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to methods and systems for adaptive ultrasound image optimization through automatic gain control adjustments, such as automatic time gain compensation (TGC) adjustments or corrections.

BACKGROUND OF THE INVENTION

Ultrasound imaging is a medical imaging technique for imaging organs and soft tissues in a human body. Ultrasound imaging uses real time, non-invasive high frequency sound waves to produce two-dimensional (2D) and/or three-dimensional (3D) images.

In some instances, measures may be taken to enhance ultrasound images. For example, ultrasound image quality may be enhanced by adjusting such things as overall gain, time gain compensation (TGC), lateral gain compensation (LGC), dynamic range, frequency, etc. In this regard, time gain compensation (TGC) may be applied to ultrasound images, to enhance image quality, by accounting for attenuation caused by tissues being imaged. By increasing received signal intensity with depth, artifacts in the uniformity of image intensity may be reduced. Further, LGC can be used to enhance the image quality by adjusting gain setting as a function of lateral scan position.

In many ultrasound systems enhancing image quality may typically be done based on user input and/or interactions. For example, to get optimum image quality the user may have to adjust several controls (e.g., controls relating to overall gain, TGC, LGC, dynamic range, frequency, etc.) Reaching an optimum arrangement of the controls may require significant interactions between the user and this system. Undertaking such extensive interactions may be uncomfortable and/or time-consuming, and as a result users may forgo attempts to identify these optimum arrangements, and consequently would not truly optimize the images as often and simply work with less optimal images.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for adaptive ultrasound image optimization through automatic TGC control adjustment, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
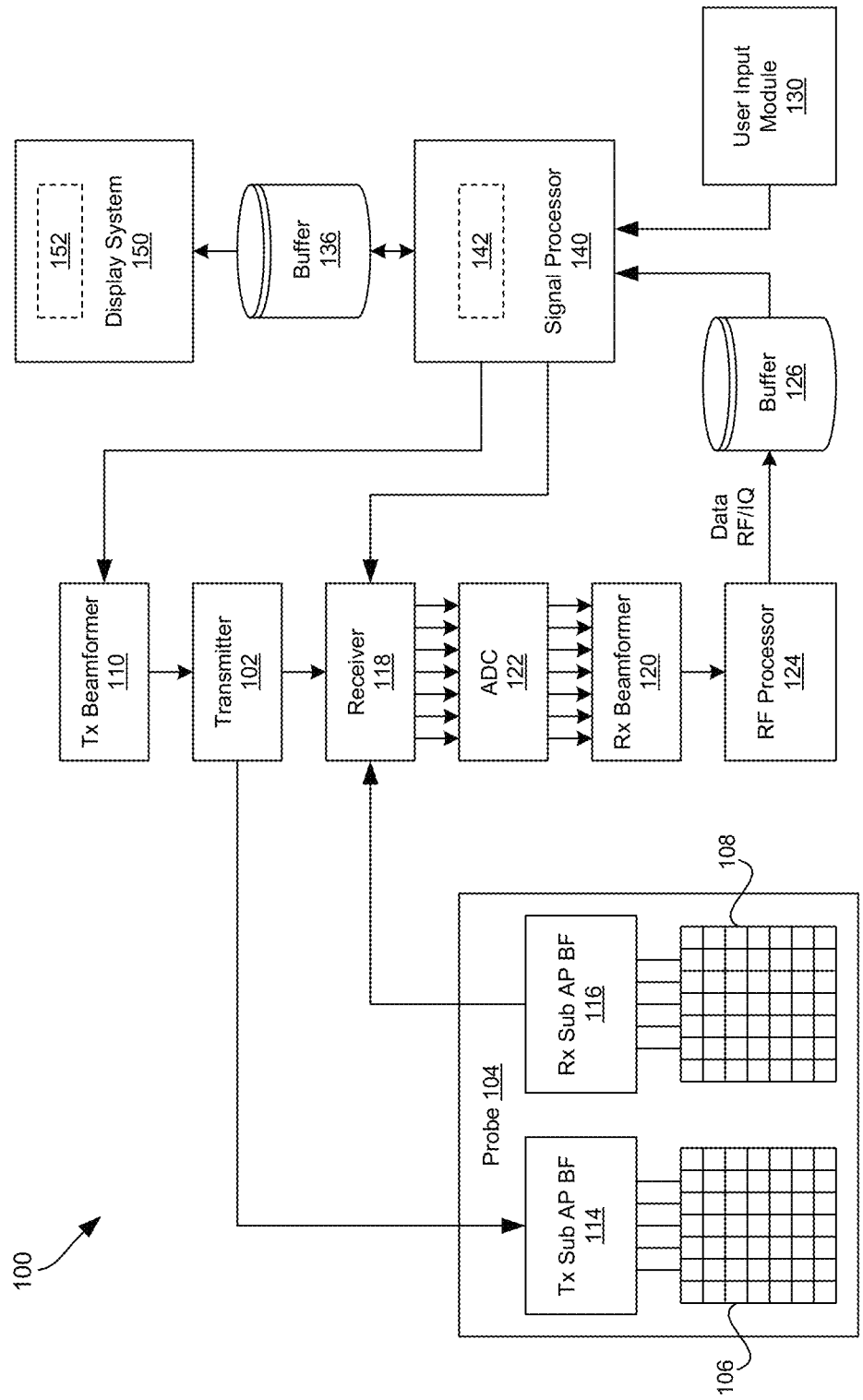
FIG. 1 is a block diagram illustrating an example ultrasound system that is operable to provide adaptive ultrasound image optimization through automatic gain adjustment, in accordance with an embodiment of the invention.

Certain embodiments of the invention may be found in methods and systems for providing adaptive ultrasound image optimization, particularly through automatic gain compensation (e.g., TGC and/or LGC), such as by determining and applying optimal gain to ultrasound images; determining settings for user controls relating to the gain compensation parameters (e.g., TGC user controls) corresponding to the determined optimal gain (values); and providing feedback to users relating to the determined settings for the TGC user controls.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments of the present invention where the data is represented by a "voxel." Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or submodes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmit event (e.g., synthetic aperture techniques).

In various embodiments, ultrasound processing to form images is performed, including time gain compensation (TGC) auto-corrections, for example, in software, firmware, hardware, or a combination thereof. One implementation of an ultrasound system in accordance with various embodiments is illustrated in FIG. 1.

FIG. 1 is a block diagram illustrating an example ultrasound system that is operable to provide adaptive ultrasound image optimization through automatic gain adjustment, in accordance with an embodiment of the invention. Shown in FIG. 1 is an ultrasound system 100.

The ultrasound system 100 comprises, for example, a transmitter 102, an ultrasound probe 104, a transmit beamformer 110, a receiver 118, a receive beamformer 120, a RF processor 124, a RF/IQ buffer 126, a user input module 130, a signal processor 140, an image buffer 136, and a display system 150.

The transmitter 102 may comprise suitable circuitry that may be operable to drive an ultrasound probe 104. The transmitter 102 and the ultrasound probe 104 may be implemented and/or configured for one dimensional (1D), two dimensional (2D), and/or three dimensional (3D) ultrasound scanning. In this regard, ultrasound probe 104 may comprise 1D or 2D array of piezoelectric elements. For example, as shown in FIG. 1, the ultrasound probe 104 may comprise a group of transmit transducer elements 106 and a group of receive transducer elements 108, that normally constitute the same elements. The transmitter 102 may be driven by the transmit beamformer 110. The transmit beamformer 110 may comprise suitable circuitry that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like).

The group of transmit transducer elements 106 can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet." The transmitted ultrasonic signals may be back-scattered from structures in the object of interest, like tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118.

The receiver 118 may comprise suitable circuitry that may be operable to receive and demodulate the signals from the probe transducer elements or receive sub-aperture beamformer 116. The demodulated analog signals may be communicated to one or more of the plurality of A/D converters (ADCs) 122.

Each plurality of A/D converters 122 may comprise suitable circuitry that may be operable to convert analog signals to corresponding digital signals. In this regard, the plurality of A/D converters 122 may be configured to convert demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable circuitry that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable circuitry that may be operable to demodulate the RF signals. In accordance with an embodiment of the invention, the RF processor 124 may comprise a complex demodulator (not shown) that is operable to demodulate the RF signals to form In-phase and quadrature (IQ) data pairs (e.g., B-mode and color IQ data pairs) which may be representative of the corresponding echo signals. The RF or IQ signal data may then be communicated to an RF/IQ buffer 126.

The RF/IQ buffer 126 may comprise suitable circuitry that may be operable to provide temporary storage of output of the RF processor 124—e.g., the RF or IQ signal data, which is generated by the RF processor 124.

The user input module 130 may comprise suitable circuitry that may be operable to enable obtaining or providing input to the ultrasound system 100, for use in operations thereof. For example, the user input module 130 may be used to input patient data, surgical instrument data, scan parameters, settings, configuration parameters, change scan mode, and the like. In an example embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 140, the image buffer 136, and/or the display system 150.

The signal processor 140 may comprise suitable circuitry that may be operable to process the ultrasound scan data (e.g., the RF and/or IQ signal data) and/or to generate corresponding ultrasound images, for presentation on a display system 150. The signal processor 140 is operable to perform one or more processing operations according to a plurality of selectable ultrasound modalities on the acquired ultrasound scan data. In some instances, the signal processor 140 may be operable to perform compounding, motion tracking, and/or speckle tracking. Acquired ultrasound scan data may be processed in real-time during a scanning session as the color flow and B-mode echo signals are received. Additionally or alternatively, the ultrasound scan data may be stored temporarily in the RF/IQ buffer 126 during a scanning session and processed in less than real-time in a live or off-line operation.

In operation, the ultrasound system 100 may be used in generating ultrasonic images, including two-dimensional (2D) and/or three-dimensional (3D) images. In this regard, the ultrasound system 100 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 150 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

In some instances, the ultrasound system 100 may be configured to support grayscale and color based operations. For example, the signal processor 140 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 136 and/or the display system 150. The color processing may comprise processing color based RF signal data or IQ data pairs to form frames to overlay on B-mode frames that are provided to the image buffer 136 and/or the display system 150. The grayscale and/or color processing may be adaptively adjusted based on user input—e.g., a selection from the user input module 130, for example, for enhance of grayscale and/or color of particular area.

In various implementations, the ultrasound system 100 may support adaptive image quality enhancement. For example, the ultrasound system 100 may be configured to enable enhancing quality of ultrasound images, such as by allowing for adjusting various parameters such as overall gain, dynamic range, frequency, time gain compensation (TGC), lateral gain compensation (LGC), etc. In this regard, gain may be adjusted, typically after beamforming, with gain adjustments comprising, for example, TGC gain adjustments, which may be adjustments in the axial direction carried out by increasing or decreasing gain as a function of depth, and/or LGC gain adjustments, which may be adjustments to gain settings as function of lateral scan position.

The ultrasound system 100 may incorporate user controls (e.g., as part of the user input module 130) for adjusting parameters relating to image quality, such as overall gain, TGC, LGC, dynamic range, frequency, and the like. Users of the ultrasound system 100 may then attempt to determine or identify optimum arrangement(s) of the user controls to achieve desired/optimal enhancement of the images. Reaching or determining these arrangements may require, however, significant interactions between the user and the ultrasound system 100. Such extensive interactions may be uncomfortable and/or time-consuming, and consequently users may forgo attempts to identify these optimum arrangements, and as a result images may not be as optimized often forcing users (or others using the images) to work with less optimal images.

Accordingly, image quality optimization may be achieved in enhanced manner, by incorporating means for addressing such issues, such as by using automatic optimization. Further, to enhance operability of ultrasound systems, rather than simply applying automatic optimization strategies without representing the optimization on the user controls, ultrasound systems may be configured to support transitions into optimization states in which internal corrections may be applied, and the optimization outcome may be represented on the available user controls. Accordingly, the ultrasound systems may not only be operable to apply automatic optimized corrections, but may also be operable to provide feedback to the users, particularly with respect to arrangements (e.g., settings) of pertinent user control corresponding to optimal corrections. This may also allow users to apply optimal user control settings in certain future use scenarios (e.g., when performing ultrasound imaging on the same patients and/or organs).

For example, in various embodiments of the invention, ultrasound systems (e.g., the ultrasound system 100) may be configured to support automatic gain compensation (e.g., TGC and/or LGC) correction/optimization, and to support providing feedback to users relating to user controls arrangements for achieving optimal TGC in the systems.

For example, as noted above, enhancing image quality may comprise application of time gain compensation (TGC) to captured (or generated) images. The application of TGC may typically be carried out by adjusting various TGC parameters, to adjust the TGC gain. This is typically done manually by the user, using a plurality of user controls. The plurality of user controls may comprise, for example, sliders, turning knobs, etc. Each of the user controls may be adjusted manually by the user to set or modify a particular TGC related parameter.

In various embodiments of the present invention, image quality optimization may be achieved by application of automatic corrections to received or generated ultrasound images. For example, the signal processor 140 may comprise an auto-correction module 142, which may comprise suitable circuitry for determining and/or applying optimization corrections to ultrasound images generated by the ultrasound system 100. The auto-correction module 142 may take as input, for example, ultrasound images; may determine for these images possible optimization or correction adjustments; and may apply the optimization or correction adjustments. In this regard, the auto-correction module 142 may determine the optimization or correction adjustments based on analysis of the input images, and/or based on pre-programmed optimization/correction characteristics (and/or parameters or criteria pertinent thereto). Further, in addition to applying the optimization/correction adjustments, the auto-correction module 142 may be configured to provide control functions based on the adjustments and/or to provide feedback to users relating to the adjustments. For example, the auto-correction module 142 may be configured to determine settings of available user control relating to the applied adjustments, and/or may provide feedback to users regarding the determined settings.

In an example embodiment of the invention, the ultrasound system 100 may be operable to apply automatic TGC corrections to received or generated ultrasound images. For example, the auto-correction module 142 may be configured to automatically determine and apply optimal TGC gain to ultrasound images. The auto-correction module 142 may receive ultrasound images as input, for example, and may process the ultrasound images to determine corresponding TGC gain for application to the ultrasound images. In this regard, the auto-correction module 142 may determine (or estimate) based on analysis of the input ultrasound images a corresponding TGC curve associated with the processed images. The TGC gain may then be selected or identified based on the TGC curve, for application to the ultrasound images. The auto-correction module 142 may determine or estimate the TGC curve, and/or may select the TGC gain, based on pre-programmed control information. For example, the pre-programmed control information may relate to pre-set target characteristics (e.g., brightness, contrast, etc.) in the ultrasound images. Thus, pre-set target characteristics may be used in analyzing the input images (e.g. in determining whether the images meet these characteristics, and if no, to determine what changes may be needed to do so) to determine or estimate the corresponding TGC curve, and to select the TGC gain from that curve.

Further, in some instances the estimated TGC curve (and the optimal TGC gain or other adjustments based thereon) may be used to determine corresponding settings for each of the TGC related controls available to the user (turning knobs, sliders, etc.) These settings may then be shown (or otherwise provided) to the user, thus making corresponding control arrangements (corresponding to the optimal TGC) known and available to the user (e.g., for future use, where possible). Hence, the automatic gain adjustments become transparent to the user making the automatic gain correction user interface more intuitive. For example, in instances where the ultrasound system 100 may utilize TGC sliders, these sliders may be adjustable automatically by the system when applying the TGC auto-correction procedure. The user would then learn of the settings (e.g., position) of each of the TGC slider for future reference. With mechanical controls (e.g., sliders, turning knobs, etc.) the system may be configured to enable such feedback when applying automatic correction. The ultrasound system 100 may incorporate motors to move the controls to position them automatically.

In another example embodiment of the invention, the ultrasound system 100 may be operable to apply automatic LGC corrections to ultrasound images, substantially in similar manner as described above with respect to TGC corrections. In this regard, lateral gain compensation may be used to adjust gain applied to images as a function of lateral position. In this regard, when applying LGC, gain may be controlled in small sectors (e.g., user selected) across the image to which LGC is applied. TGC may be implemented and/or performed at the same point as TGC in the processing path. As with TGC, suitable user controls may be incorporated to enable a user to control LGC—that is to allow the user to adjust gain setting in the lateral position. For example, such user controls may allow the user to select portions of the image to which LGC is applied, and/or to set or adjust LGC related parameters. Also, as with TGC, LGC gain (including optimal LGC gain) may be determined substantially in the same manner as described above with respect to TGC—e.g., based on a corresponding LGC curve, which may be determined or estimated, such as based on processing of the images. Accordingly, in some embodiments, the auto-correction module 142 may be configured to automatically determine and apply optimal LGC gain corrections to ultrasound images, and/or to provide user feedback (e.g., with respect to corresponding available LGC user controls), substantially as described above with respect providing automatic TGC gain adjustment/corrections.

In some implementations, at least some user controls may not be physical—that is they may be 'virtual'. For example, the display system 150 may be configured to support user interactions (e.g., by incorporating a touch-screen), providing a user control interface 152, which may be used to display visual user controls (e.g., sliders) with which the user may interact (e.g., by touching or moving his/her fingers on the touch-screen) to provide input. Accordingly, during auto-corrections the virtual user controls may also be automatically adjusted to show the arrangement(s) corresponding to the optimal settings. An example of virtual user controls and use thereof in conjunction with TGC auto-correction is described in more detail below.

Automatic gain optimization (auto-correction) may be triggered or initiated in various ways. For example, TGC auto-correction may be carried on in response to particular triggers or conditions. In this regard, there one or more trigger events may be pre-defined or pre-configured, and whenever one of these trigger events occurs, the ultrasound system may transition to a particular state (e.g., an "automatic TGC mode") in which image optimization (including TGC auto-correction) may be carried out. The trigger event may comprise, for example, a user event, which may be direct (e.g., pressing dedicated optimization button) or indirect (e.g., undertaking particular action that imply desired for optimization, such adjusting depth of field, focus depth, etc.).

Image optimization (including TGC auto-correction) may be also triggered by the system, such as on regular basis (periodically) to provide a continuous optimization of the images. Once triggered, TGC auto-correction may be performed. In this regard, the TGC auto-correction may comprise performing an estimation of the optimum TGC curve, as soon as the required image data are available. The optimized TGC curve may then be converted to a user control configuration, which may comprise the overall gain and the corresponding TGC control settings (e.g., TGC slider positions) approximating the optimum TGC curve. The user control configuration may then be applied to the user controls/interface while also applying it (or more particularly the determined optimal TGC) to the ultrasound images. In instances where continuous optimization is being performed, some temporal filtering may be applied to the calculated user control configurations, to keep the change of the ultrasound images continuous. In addition to the TGC optimization one could also optimize other parameters like dynamic range, etc.

Similarly, LGC auto-correction may also be triggered in substantially similar manner—e.g., in response to user or system triggered events that transition the system to particular corresponding state (e.g., an "automatic LGC mode.")

Figure 2:
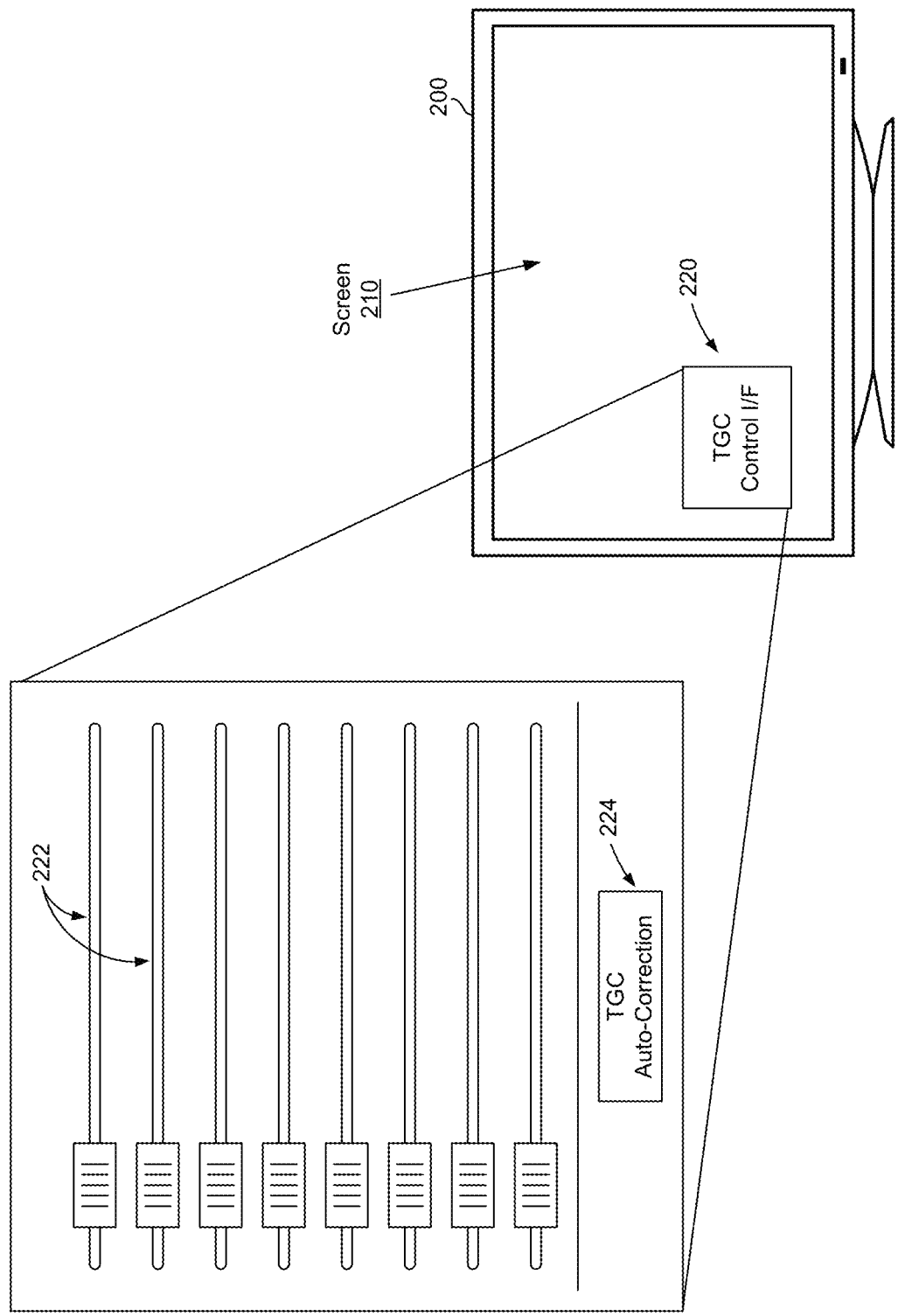
FIG. 2 is a block diagram illustrating use of on-screen virtual TGC sliders in an ultrasound system, in accordance with an embodiment of the invention.

FIG. 2 is a block diagram illustrating use of on-screen virtual TGC sliders in an ultrasound system, in accordance with an embodiment of the invention. Shown in FIG. 2 is a display system 200.

The display system 200 may be configurable to display images (on screen 210). In particular, the display system 200 may be utilized to display ultrasound images. For example, the display system 200 may correspond to the display system 150 of the ultrasound system 100 of FIG. 1, thus allowing for displaying ultrasound images (2D or 3D) that are generated via the ultrasound system 100 during ultrasound scans. In some instances, the display system 200 may be configured to support or perform, in addition to displaying ultrasound images, additional functions and/or operations. For example, the display system 200 may be configured to support displaying other information or visual effects other than the images (e.g., ultrasound images) being displayed on the screen 210. Such additional information or visual effects may be, for example, displayed on part of the screen 210 (being superimposed on part of the ultrasound image, for example). Further, the display system 200 may be configured to enable obtaining or receiving user input, such as by means of interacting with the screen 210 (e.g., the screen 210, or at least portion thereof, being implemented as 'touch-screen'). Accordingly, the display system 200 may support interactions with system users. For example, the display system 200 may be configured to support displaying information or visual elements, and/or for enabling user interactions in conjunction with various functions or operations, such as gain adjustments or corrections.

In an example embodiment of the invention, the display system 200 may be configured to support displaying information or visual elements, and/or for enabling user interactions in conjunction with time gain compensation (TGC) corrections. For example, the display system 200 may display on a section of the screen 210 a time gain compensation (TGC) control interface (I/F) 220. The TGC control I/F 220 may be used to enable interactions with the user with respect to time gain compensation (TGC) corrections to displayed ultrasound images. In particular implementations, such as when the screen 210 of the display 200 may be configurable as touch-screen (thus allowing 'receiving' input from the user by touching parts of the screen 210), the TGC control I/F 220 may be configured to enable user interactivity with respect to automatic TGC corrections in the ultrasound system.

For example, the TGC control I/F 220 may comprise a plurality of sliders 222, and a TGC auto-correction button 224. In this regard, the plurality of sliders 222 may be 'virtual' (rather than physical) sliders, in the sense that each slider may be a visual effect, with the slider being 'moved' in response to the user sliding his/her finger on the image of that slider on the screen 210, with the TGC control I/F 220. Each of the plurality of sliders 222 may correspond to particular parameter or setting associated with time gain compensation. Thus TGC correction may be applied differently by varying (sliding) each of the plurality of sliders 222. The TGC auto-correction button 224 may allow the user to request, instruct, or trigger automatic time gain compensation (TGC) corrections. In this regard, the TGC auto-correction button 224 may be 'virtual' (rather than physical) button, in the sense that it may be a visual effect, with the TGC auto-correction being triggered in response to the user pressing his/her finger on the image of that button on the screen 210, with the TGC control I/F 220. The automatic time gain compensation (TGC) corrections may be performed, for example, in accordance with preset or pre-configured TGC curves, as described with respect to FIG. 1. Example use scenarios of the TGC control I/F 220 are described in more detail below, such as with respect to FIG. 3.

While the example implementation depicted in FIG. 2 relates to providing an interface for facilitating user interactions in conjunction with time gain compensation (TGC) corrections, it should be understood that the disclosure is not so limited, and that similar implementations may be utilized in substantially similar manner with respect to other functions or operations, such as lateral gain compensation (LGC) corrections for example.

Figure 3:
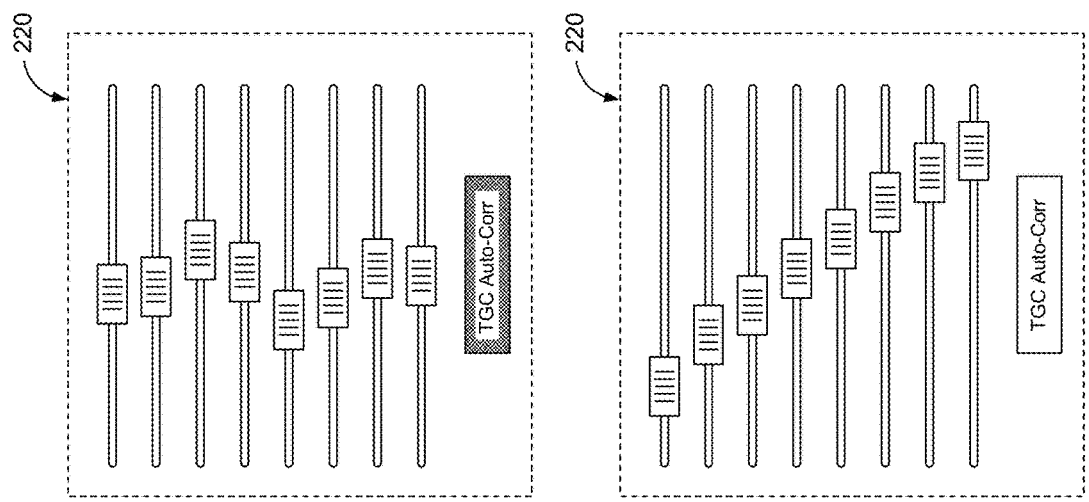
FIG. 3 is a block diagram illustrating example use scenario of on-screen virtual TGC sliders on screen when applying TGC adjustments, in accordance with an embodiment of the invention.
Figure 3:
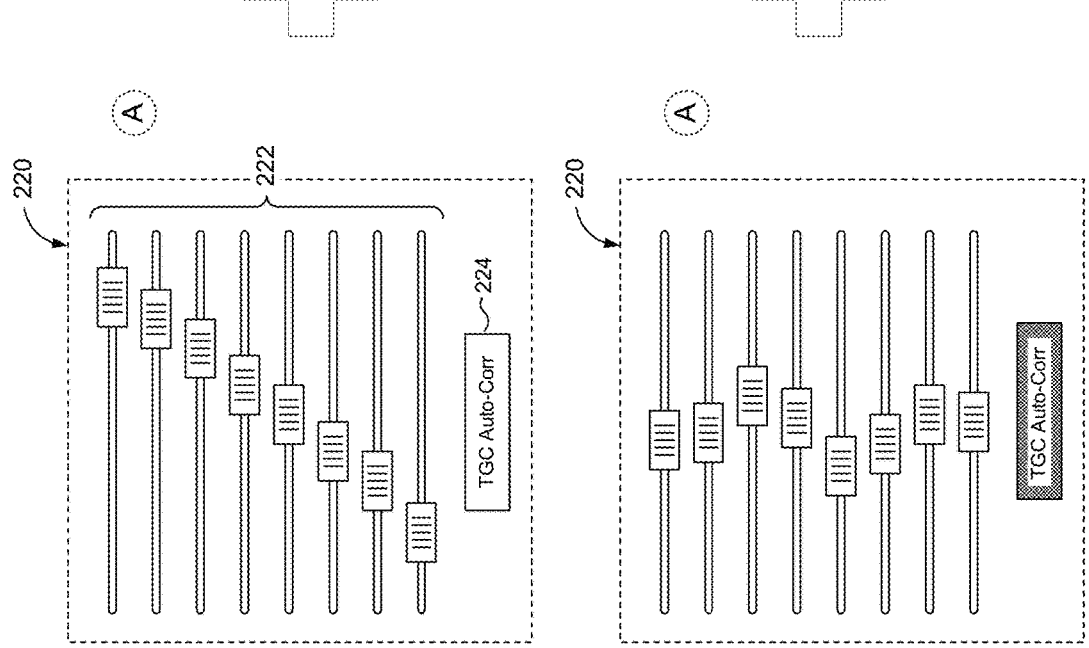

FIG. 3 is a block diagram illustrating example use scenario of on-screen virtual TGC sliders on screen when applying TGC adjustments, in accordance with an embodiment of the invention.

In example use scenario 310, the TGC control I/F 220 is in an initial state A, corresponding to particular TGC correction corresponding to a particular combination of settings for applicable TGC parameters (each of which being represented by and/or corresponding to one of the plurality of 'virtual' sliders 222. For example, state A in scenario 310 may correspond to a particular manual TGC correction, resulting from the user manually selecting particular setting for each of the TGC parameters, by individually sliding each of the plurality of 'virtual' sliders 222. In subsequent state B, automatic TGC correction may be triggered, such as by the user. For example, the user may trigger automatic TGC correction by pressing the 'virtual' TGC auto-correction button 224. The automatic TGC correction may then be performed. In this regard, the automatic TGC correction may correspond to the optimal TGC, which may be determined based on a pre-determined TGC optimization curve for example. Further, the setting for each of the TGC parameters, corresponding to the optimal TGC, may be determined. The TGC control I/F 220 may then be adjusted to provide feedback to the user based on the applied optimal TGC. In particular, the plurality of 'virtual' sliders 222 may display the setting of each TGC parameter corresponding to the optimal TGC, by adjusting the position of the corresponding one of the plurality of 'virtual' sliders 222 based on the setting of the associated TGC parameters. In other words, as shown in FIG. 3, the positions of the plurality of 'virtual' sliders 222 in state B of scenario 310 are adjusted (and displayed) based on the determined settings of the TGC parameters for the optimal TGC. Further, in some instances, an indication that the displayed positions corresponding to optimal TGC may be provided to the user. For example, the 'virtual' TGC auto-correction button 224 may be modified (once the automatic TGC correction is trigged and applied) to show that, such as by changing its color or shape, for example. The indication may also be provided by other means, such as by provide textual output message (e.g., within the TGC control I/F 220, or somewhere else in the screen 210).

In example use scenario 320, the TGC control I/F 220 may be in an initial state A, which may correspond to the (prior) application of automatic TGC correction. Thus, state A of scenario 320 may correspond to the subsequent state B in scenario 310. Accordingly, in state A of the scenario 320, positions of the plurality of 'virtual' sliders 222 would represent the settings of the TGC parameters corresponding to the optimal TGC. Further, the 'virtual' TGC auto-correction button 224 may indicate (e.g., based on its color or shape) that the present setting of the plurality of 'virtual' sliders 222 correspond to the optimal TGC. In a subsequent state B, the user may effectuate manual TGC correction, corresponding to a particular, manually selected combination of applicable TGC parameters, resulting from the user manually selecting particular setting for each of the TGC parameters, by individually sliding each of the plurality of 'virtual' sliders 222 (from the setting of the optimal TGC). Further, the 'virtual' TGC auto-correction button 224 may now indicate (e.g., by change in its color or shape) that the present setting of the plurality of 'virtual' sliders 222 correspond to the manually selected TGC settings.

While the example user scenarios described with respect in FIG. 3 relate to applying time gain compensation (TGC) adjustments via a user interface implemented in accordance with an example embodiment of the invention, it should be understood that the disclosure is not so limited, and that similar implementations may be utilized in substantially similar manner with respect to other functions or operations, such as lateral gain compensation (LGC) corrections for example.

Figure 4:
FIG. 4 illustrates example use of automatic TGC correction to enhance an ultrasound image that is generated based on default TGC gain, in accordance with an embodiment of the invention.
Figure 4:

FIG. 4 illustrates example use of automatic TGC correction to enhance an ultrasound image that is generated based on default TGC gain, in accordance with an embodiment of the invention. Shown in FIG. 4 are ultrasound images 410 and 420.

The ultrasound image 410 may represent an example ultrasound image of particular organ (for particular patient). Further, the ultrasound image 410 may represent the ultrasound image as generated with default TGC gain. The default TGC gain may correspond to, for example, particular default combination of the applicable TGC parameters (available in the ultrasound system). For example, with reference to the implementation described in FIG. 2, the default TGC gain may correspond to each of the plurality of 'virtual' sliders 222 at the left-most position (representing the minimum setting for the corresponding TGC parameters).

The ultrasound image 420 may represent the result of the application of automatic TGC correction to the same ultrasound image—that is ultrasound image 410. For example, the ultrasound image 420 may result from triggering automatic TGC correction, such as by pressing the 'virtual' TGC auto-correction button 224. Accordingly, as a result of application of automatic TGC correction, the quality of the ultrasound image may be enhanced.

Figure 5:
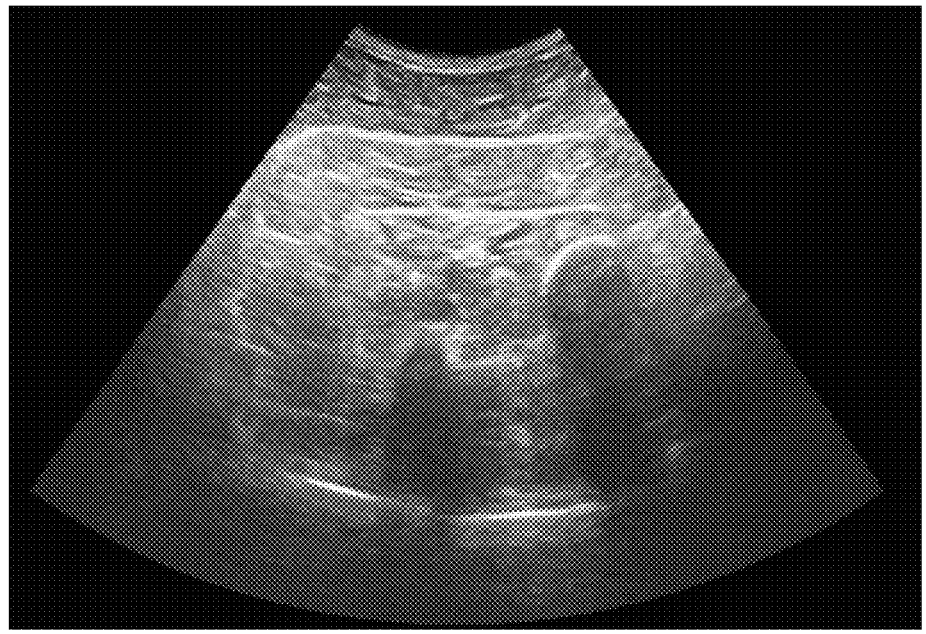
FIG. 5 illustrates example use of automatic TGC correction to enhance an ultrasound image that is generated based on user set TGC gain, in accordance with an embodiment of the invention.
Figure 5:

FIG. 5 illustrates example use of automatic TGC correction to enhance an ultrasound image that is generated based on user set TGC gain, in accordance with an embodiment of the invention. Shown in FIG. 5 are ultrasound images 510 and 520.

The ultrasound image 510 may represent an example ultrasound image of particular organ (for particular patient). Further, the ultrasound image 510 may represent the ultrasound image as generated with user-specified TGC gain. In this regard, the user-specified TGC gain may correspond to, for example, particular combination of the applicable TGC parameters (available in the ultrasound system) that is manually selected or set by the user. For example, with reference to the implementation described in FIG. 2, the user-specified TGC gain may correspond to a combination of settings for applicable TGC parameters corresponding to manually selected or set positions for the plurality of 'virtual' sliders 222. Thus, the ultrasound image 510 may correspond to configuring or altering of ultrasound images based on user set TGC gain.

The ultrasound image 520 may represent the result of the application of automatic TGC correction to the same ultrasound image—that is ultrasound image 510. For example, the ultrasound image 520 may result from triggering automatic TGC correction, such as by pressing the 'virtual' TGC auto-correction button 224. Accordingly, as a result of application of automatic TGC correction, the quality of the ultrasound image may be enhanced.

Figure 6:
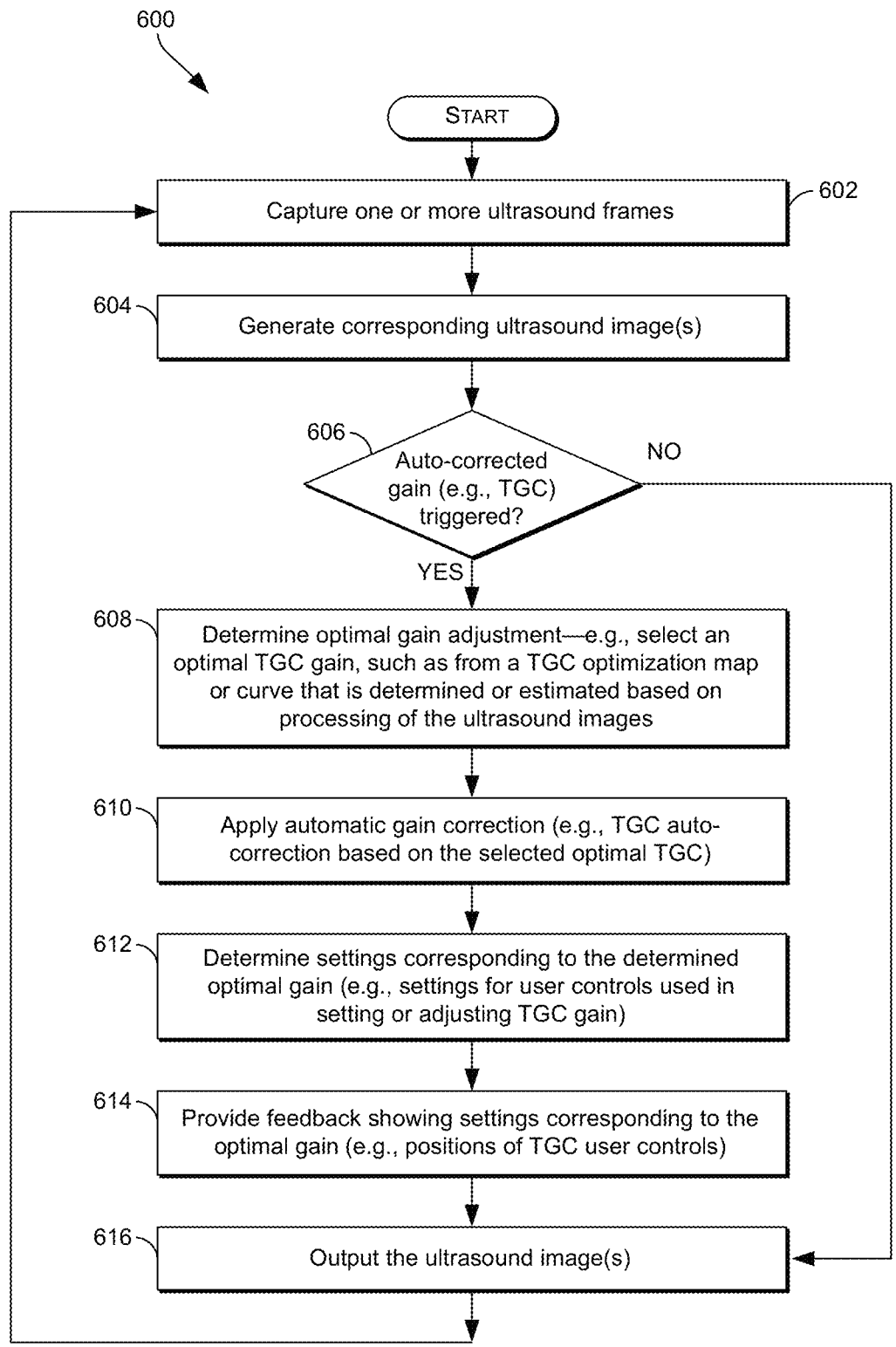
FIG. 6 is a flow chart illustrating example steps that may be utilized for providing adaptive ultrasound image optimization through automatic gain corrections, in accordance with an embodiment of the invention.

FIG. 6 is a flow chart illustrating example steps that may be utilized for providing adaptive ultrasound image optimization through automatic gain corrections, in accordance with an embodiment of the invention. Shown in FIG. 6 is a flow chart 600, which comprises a plurality of example steps.

It should be understood, however, that certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 602, data corresponding to a sequence of ultrasound frames may be obtained, such as using an ultrasound system (e.g., the ultrasound system 100 of FIG. 1). The ultrasound frames may be 2D and/or 3D frames.

In step 604, ultrasound images may be generated, such as based on processing of the obtained ultrasound data. The processing may comprise grayscale B-mode processing and/ or color processing. Further, in some instances, the processing may comprise applications of various enhancements to the images, which include application of gain or adjustments thereof (e.g., time gain compensation (TGC), lateral gain compensation (LGC), etc.).

In step 606, it may be determined whether gain autocorrections (e.g., TGC auto-correction, LGC auto-correction, etc.) are triggered. In this regard, gain auto-corrections may be triggered in response to system pre-configuration, user input/commands, etc. In instances where no gain autocorrections are triggered, the process may jump to step 614; otherwise the process may proceed to step 608.

In step 608, the optimal gain auto-correction (and/or parameters or criteria relating thereto) may be determined or selected. For example, an optimal TGC gain may be selected, such as from a TGC optimization map or curve which may be determined or estimated based on, for example, processing of the ultrasound images.

In step 610, optimal gain auto-correction may be applied to the ultrasound image(s), such as based on the parameters (or criteria) determined in the previous step. For example, TGC auto-correction may be applied to the ultrasound image(s), based on the optimal TGC determined in the previous step (e.g., from the estimated TGC curve).

In step 612, settings (e.g., for available user controls) corresponding to the optimal gain auto-correction (or application thereof) may be determined. For example, settings for user controls used in setting or adjusting TGC, corresponding to the determined optimal TGC, may be determined.

In step 614, feedback showing settings corresponding to the optimal gain auto-correction (e.g., optimal TGC) may be provided. In this regard, the feedback may indicate or show the positions of available user controls in the system (e.g., sliders, knobs, buttons, or the like; physical or virtual) corresponding to optimal gain (or adjustment thereof). For example, when applying TGC auto-corrections, and where a plurality of sliders is used to adjust settings of various TGC parameters, the feedback may comprise showing the respective position of each slider corresponding to the optimal TGC (which had been applied).

In step 616, the ultrasound image(s), which may be gain auto-corrected, may be displayed. The process may then loop back to step 602, to continue handling additional ultrasound data/images (or may terminate if the operation of the ultrasound system is ceased).

As utilized herein the term "circuitry" refers to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or." As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "example" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing sequential needle recalibration by correlating a sequence of calibration data for a tracking system to a plurality of corresponding ultrasound probe positions.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
   applying by a processor of an ultrasound system, gain optimization or correction in an automatic gain mode, the applying of the gain optimization or correction in the automatic gain mode comprises:
      determining optimal gain based on one or more input ultrasound images;
      determining based on the optimal gain, settings for a plurality of user controls of the ultrasound system, corresponding to the optimal gain, wherein the plurality of user controls are adjustable manually and automatically; and
      providing feedback to a user of the ultrasound system, wherein:
         the feedback relates to the settings for the plurality of user controls which correspond to the optimal gain; and
         providing the feedback comprises visually showing each of the plurality of user controls set at a position corresponding to the optimal gain as determined based on the one or more input ultrasound images.

2. The method of claim 1, wherein applying the gain optimization or correction in the automatic gain mode further comprises:
   determining adjustments corresponding to the optimal gain; and
   applying the adjustments to one or more ultrasound images outputted via a display of the ultrasound system.

3. The method of claim 1, comprising determining at least some of the settings for the plurality of user controls of the ultrasound system, and/or at least some adjustments, for the optimal gain based on one or more optimal gain maps or curves.

4. The method of claim 1, comprising triggering the gain optimization or correction in the automatic gain mode based on user input or action.

5. The method of claim 1, comprising applying the gain optimization or correction in the automatic gain mode continuously.

6. The method of claim 1, wherein the plurality of user controls comprises a plurality of physical controls, and each of the plurality of physical controls is configured to enable adjusting at least one parameter associated with adjustments.

7. The method of claim 6, wherein the plurality of physical controls comprises physical sliders and/or rotating knobs.

8. The method of claim 1, wherein the plurality of user controls comprises a plurality of virtual controls, and each of the plurality of virtual controls is configured to enable adjusting at least one parameter associated with adjustments.

9. The method of claim 8, wherein the plurality of virtual controls comprises virtual sliders and/or rotating knobs on a touch-screen.

10. The method of claim 1, wherein providing feedback to the user of the ultrasound system comprises adjusting each of the plurality of user controls to a position corresponding to the settings recommended for the optimal gain.

11. The method of claim 1, wherein the gain optimization or correction comprises at least one of time gain compensation (TGC) and lateral gain compensation (LGC).

12. A system, comprising:
an ultrasound device that comprises a processor operable to apply gain optimization or correction in an automatic gain mode, the applying of the gain optimization or correction in the automatic gain mode comprises:
determining optimal gain based on one or more input ultrasound images;
determining based on the optimal gain, settings for a plurality of user controls of the ultrasound device, corresponding to the optimal gain, wherein the plurality of user controls are adjustable manually and automatically; and
providing feedback to a user of the ultrasound device, wherein:
the feedback relates to the settings for the plurality of user controls that correspond to the optimal gain; and
providing the feedback comprises visually showing each of the plurality of user controls set at a position corresponding to the optimal gain as determined based on the one or more input ultrasound images.

13. The system of claim 12, wherein applying the gain optimization or correction in the automatic gain mode further comprises:
determining adjustments corresponding to optimal gain; and
applying the adjustments to one or more ultrasound images outputted via a display of the ultrasound device.

14. The system of claim 12, wherein the processor is operable to determine at least some of the settings for the plurality of user controls of the ultrasound device, and/or at least some adjustments, for the optimal gain based on one or more optimal gain maps or curves.

15. The system of claim 12, wherein the gain optimization or correction in the automatic gain mode is triggered based on user input or action.

16. The system of claim 12, wherein the processor is operable to apply the gain optimization or correction in the automatic gain mode continuously.

17. The system of claim 12, wherein the plurality of user controls comprises a plurality of physical controls, and each of the plurality of physical controls is configured to enable adjusting at least one parameter associated with adjustments.

18. The system of claim 17, wherein the plurality of physical controls comprises physical sliders and/or rotating knobs.

19. The system of claim 12, wherein the plurality of user controls comprises a plurality of virtual controls, and each of the plurality of virtual controls is configured to enable adjusting at least one parameter associated with adjustments.

20. The system of claim 19, wherein the plurality of virtual controls comprises virtual sliders and/or rotating knobs on a touch-screen.

21. The system of claim 12, wherein providing feedback to the user of the ultrasound system comprises adjusting each of the plurality of user controls to a position corresponding to the settings recommended for the optimal gain.

22. The system of claim 12, wherein the gain optimization or correction comprises at least one of time gain compensation (TGC) and lateral gain compensation (LGC).

23. A non-transitory computer readable medium having stored thereon, a computer program having at least one code section, the at least one code section being executable by a machine for causing the machine to perform steps comprising:
applying during ultrasound imaging gain optimization or correction in an automatic gain mode, wherein the applying of the gain optimization or correction in the automatic gain mode comprises:
determining optimal gain based on one or more input ultrasound images;
determining based on the optimal gain, settings for a plurality of user controls, corresponding to the optimal gain, wherein the plurality of user controls are adjustable manually and automatically; and
providing user feedback, wherein:
the user feedback relates to the settings for the plurality of user controls that correspond to the optimal gain; and
providing the user feedback comprises visually showing each of the plurality of user controls set at a position corresponding to the optimal gain as determined based on the one or more input ultrasound images.

24. The non-transitory computer readable medium of claim 23, wherein applying the gain optimization or correction in the automatic gain mode further comprises:
determining adjustments corresponding to the optimal gain; and
applying the adjustments to one or more ultrasound images outputted via a display of the ultrasound system.

25. The non-transitory computer readable medium of claim 23, comprising determining at least some of the settings for the plurality of user controls of the ultrasound system, and/or at least some adjustments, for the optimal gain based on one or more based on one or more optimal gain maps or curves.

26. The non-transitory computer readable medium of claim 23, wherein the plurality of user controls comprises a plurality of virtual controls, and each of the plurality of virtual controls is configured to enable adjusting at least one parameter associated with adjustments.

27. The non-transitory computer readable medium of claim 23, wherein providing user feedback relating to the settings for the plurality of user controls comprises adjusting each of the plurality of user controls to a position corresponding to the settings recommended for the optimal gain.

28. The non-transitory computer readable medium of claim 23, wherein the gain optimization or correction comprises at least one of time gain compensation (TGC) and lateral gain compensation (LGC).

* * * * *